United States Patent
Schatz et al.

(10) Patent No.: US 10,118,851 B2
(45) Date of Patent: Nov. 6, 2018

(54) PROCESS FOR THE ANAEROBIC FERMENTATION OF BIOGENIC WASTE MATERIALS AND PLANT FOR CARRYING OUT THIS PROCESS

(71) Applicant: HITACHI ZOSEN INOVA AG, Zürich (CH)

(72) Inventors: Adrian Schatz, Niederwangen (CH); René Leisner, Constance (DE)

(73) Assignee: HITACHI ZOSEN INOVA AG, Zürich (CH)

(*) Notice: Subject to any disclaimer, the term of this patent is extended or adjusted under 35 U.S.C. 154(b) by 107 days.

(21) Appl. No.: 15/225,180

(22) Filed: Aug. 1, 2016

(65) Prior Publication Data
US 2017/0029309 A1 Feb. 2, 2017

(30) Foreign Application Priority Data

Jul. 31, 2015 (EP) ..................................... 15179224

(51) Int. Cl.
| | |
|---|---|
| *C02F 11/04* | (2006.01) |
| *C12M 1/107* | (2006.01) |
| *C12M 1/00* | (2006.01) |
| *C12M 1/34* | (2006.01) |
| *C02F 11/12* | (2006.01) |
| *C12P 5/02* | (2006.01) |

(52) U.S. Cl.
CPC ............ *C02F 11/04* (2013.01); *C02F 11/121* (2013.01); *C12M 21/04* (2013.01); *C12M 29/04* (2013.01); *C12M 29/18* (2013.01); *C12M 41/36* (2013.01); *C12M 47/02* (2013.01); *C12M 47/14* (2013.01); *C12P 5/023* (2013.01); *Y02W 30/43* (2015.05); *Y02W 30/47* (2015.05)

(58) Field of Classification Search
None
See application file for complete search history.

(56) References Cited

U.S. PATENT DOCUMENTS 5,601,720 A * 2/1997 Schmid ............... C05F 17/0027
210/612
9,416,372 B2 * 8/2016 Benedek .............. B01D 61/145

FOREIGN PATENT DOCUMENTS

| | | |
|---|---|---|
| DE | 10 2005 002997 A1 | 7/2006 |
| DE | 10 2005 012367 A1 | 9/2006 |
| DE | 10 2013 018833 A1 | 5/2015 |
| EP | 0 621 336 A2 | 10/1994 |
| EP | 1 076 051 A2 | 2/2001 |
| EP | 1 095 924 A2 | 5/2001 |
| GB | 2 230 004 A | 10/1990 |
| WO | 2014/076062 A1 | 5/2014 |

OTHER PUBLICATIONS

Jing Yi et al. PLOS One; Jul. 2014, vol. 9, issue 7, e102548, pp. 1-10.*
Feb. 4, 2016 Search Report issued in European Patent Application No. 15179224.9.
Jun. 22, 2017 Third Party Observation filed in European Patent Application No. 16181249.0.

* cited by examiner

*Primary Examiner* — Vera Afremova
(74) *Attorney, Agent, or Firm* — Oliff PLC

(57) ABSTRACT

A process for the anaerobic fermentation of biogenic waste materials including the steps that a fermentation material containing the waste materials is mixed with liquid and the fermentation material suspension obtained in this manner is anaerobically fermented in a fermenter and the digest produced in the fermentation of the fermentation material suspension is dewatered of a dewatering device, wherein, with separation of press water, a press cake is obtained that has a dry matter proportion increased with respect to the digest; the press water is subjected to a solids separation, wherein a residual liquid having a dry matter proportion reduced with respect to the press water of at most 15% by weight is obtained and the residual liquid is used at least in part for the mixing according to the fermentation material step.

12 Claims, 3 Drawing Sheets

PROCESS FOR THE ANAEROBIC FERMENTATION OF BIOGENIC WASTE MATERIALS AND PLANT FOR CARRYING OUT THIS PROCESS

The invention relates to a process for the anaerobic fermentation of biogenic waste materials according to the preamble of claim 1 and also to a plant for carrying out said process according to the preamble of claim 11.

Processes for the anaerobic fermentation of biogenic waste materials, in particular of domestic, garden, agricultural and industrial wastes, are known to those skilled in the art. Such processes firstly permit an ecological waste management, secondly they are also of economic interest in view of the significant amount of biogas that can be generated thereby.

Anaerobic fermentation processes have proved superior to aerobic fermentation processes not only in the mass balance but also in the energy balance. Corresponding plants for anaerobic fermentation require relatively little space and can be operated in an odor-neutral manner, and so even locations in densely settled areas come into consideration for such plants.

Among the known anaerobic fermentation processes, in principle liquid or wet fermentation processes can be differentiated from what are termed dry fermentation processes:

Wet fermentation processes are usually carried out in one or more vertical fermenters.

A corresponding process and a corresponding plant are described, for instance in GB 2 230 004.

It is disadvantageous with such processes that heavier components of the fermentation material can sediment in the fermenter before they are completely degraded.

Consequently, owing to too short a residence time, incompletely degraded components can pass into the exit region of the fermenter, which is disadvantageous not only from the economic point of view but also from the hygienic aspect.

In what are termed the dry fermentation processes, a fermentation material having a significantly higher dry matter proportion is fermented, wherein, in this case, the fermentation material is in no way dry. In these processes, the fermentation is generally carried out in a horizontal fermenter.

For instance, in EP 0 621 336, a process is described in which biogenic wastes are fermented anaerobically in a horizontal fermenter with controlled mixing in plug-flow mode. Compared with liquid fermentation processes mentioned, the process as claimed in EP 0 621 336 is distinguished in that the fermentation material has a relatively low dry matter proportion and therefore only a relatively small volume needs to be processed. This is accompanied with the advantages that corresponding plants can be dimensioned so as to be relatively small and can be operated relatively inexpensively. In particular, owing to the high content of dry matter in the fermentation material, the volume of waste water produced is reduced.

Despite these advantages, it has been found in practice that in the case of an excessive dry matter proportion, the fermentation material cannot be transported in the desired manner in the fermenter, or only with relatively great complexity.

This disadvantage can be remedied in principle in that the fermentation material is diluted with water; however, one of the main advantages of the dry fermentation process, namely the reduction of waste water, is thereby at least largely lost.

A process according to which water is fed to the fermentation material for establishing the desired homogeneity and the desired dry matter content, is described in EP 1 076 051. According to this process, in addition to fresh water or industrial water, the press water obtained during the dewatering of the fermented material can be used for the dilution.

However, the bacterially loaded press water can only be used with restrictions for the dilution, since in the case of recirculation of the press water still having a relatively high dry matter proportion, already degraded material is additionally recirculated to the fermenter, which impairs the energy balance of the process overall. This becomes of importance, in particular in the case of repeated recirculation, since the already degraded material becomes enriched or concentrated in this case. On account of these restrictions for the use of press water, the demand for used fresh water and therefore also the amount of waste water produced during the fermentation is still relatively high also for the technology described in EP 1 076 051.

It is therefore an object of the present invention to provide a process for the anaerobic fermentation of biogenic waste materials which ensures good transportability of the fermentation material and which at the same time permits the amount of waste water produced in the process to be minimized.

In particular, according to the present invention, the advantages of known dry fermentation processes, that is to say a relatively high throughput of the fermentation material with relatively low dimensioning of the plant, are to be retained.

The invention is achieved by the process as claimed in claim 1. Preferred embodiments of the invention are defined in the dependent claims.

As claimed in claim 1, the invention relates to a process for the anaerobic fermentation of biogenic waste materials comprising the steps that a) a fermentation material containing the waste materials is mixed with liquid and the fermentation material suspension obtained in this manner is anaerobically fermented in a fermenter and b) the digest produced in the fermentation of the fermentation material suspension is dewatered by means of a dewatering device, wherein, with separation of press water, a press cake having a dry matter proportion increased with respect to the digest is obtained.

According to the invention the process now comprises the additional steps that c) the press water is subjected to a solids separation, wherein a residual liquid having a dry matter proportion reduced with respect to the press water of at most 15% by weight is obtained and d) the residual liquid is used at least in part for the mixing according to a).

In contrast to the processes known in the prior art, therefore, from the press water obtained in the dewatering, before recirculation thereof into the fermenter, a further solids fraction is separated off and the dry matter proportion is lowered in this manner to a range having a defined maximum value of 15% by weight.

Solids separators which can be used therefor are specified in more detail further below. According to a particularly preferred embodiment, a vibrating screen and/or a shaking screen is used for the solids separation according to step c).

Consequently, according to the present invention, a significant proportion of the water removed from the fermenter, after corresponding workup, is recirculated back to the fermenter, as a result of which, firstly, the demand for fresh water to be introduced can be decreased, and secondly, the amount of waste water to be disposed of can be reduced.

In the context of the present invention, the proportion of liquid which is removed from the fermentation suspension in the dewatering step is designated press water, more precisely independently of whether the liquid is actually separated off by active pressing or by passive draining from the digest.

As already mentioned in connection with the technological background of the invention, the press water has a relatively high content of organic material and is generally sludge-like. The dry matter proportion of the press water is generally in a range from 15 to 20% by weight, but, depending on the manner of dewatering or the dewatering device used therefor, it can be somewhat lower. As dewatering device, for example a screw press can be used.

The fact that the press water is subjected according to the invention to a solids separation in which a residual liquid having a dry matter proportion reduced in comparison with the press water of at most 15% by weight is obtained can ensure that in the subsequent mixing of the residual liquid with the fermentation material, an optimally transportable fermentation material suspension is obtained, and, at the same time that the recirculation of energetically low-grade material is minimized.

As does the press water, therefore the residual liquid also consists of an aqueous suspension, wherein, however, the proportion of dry matter which principally consists of organic suspended matter is lower in the residual liquid than in the press water. As mentioned, the dry matter proportion of the residual liquid is at most 15% by weight, wherein it is preferably in a range from 5 to 15% by weight, particularly preferably in a range from 5 to 10% by weight. According to the most preferred embodiment, the dry matter proportion is greater than 5% by weight and less than 10% by weight.

In order to decrease the dry matter proportion to the maximum value of 15% by weight defined according to step c), conventional dewatering devices are insufficient, for which reason, in addition, a solids separator is used. As mentioned, a screen is preferably used for the solids separation, which screen, according to a particularly preferred embodiment, comprises at least two screening stages. In this regard, it is further preferred that the solids separation proceeds using a vibrating screen and/or a shaking screen.

"Dry matter proportion", in the context of the present invention, denotes the weight fraction of the dry matter or the weight of the dry matter in terms of the total weight of the respective material. Methods for determining the dry matter proportion are known to those skilled in the art and can be carried out for instance in such a manner that the liquid proportions of the material are taken off in an oven and thereafter the weight of the remaining dry matter is determined.

The circulation of the residual liquid according to the invention firstly has the aim of diluting the fermentation material or providing an optimally transportable fermentation material suspension. The invention thus differs in principle from the process presented in EP 1 095 924, according to which press water that has a relatively high dry matter proportion and is bacterially loaded is used as inoculum material for the waste materials that are to be fermented.

Rather, for the inoculation, according to a preferred embodiment of the invention, a part of the digest, the press cake obtained in step b), the residual solid separated off in step c), or a mixture thereof, is used, as is described further below.

As in EP 1 095 924, in DE 10 2005 012 367, also, there is no disclosure of a solids separation for obtaining a residual liquid having a dry matter proportion of at most 15% by weight, that is reduced in comparison with the press water. Rather, in DE 10 2005 012 367, also, the process water produced here is used for mashing or inoculation which, as in the case of EP 1 095 924, demands a relatively high dry matter proportion.

As is likewise shown in detail further below, the recirculation of the residual liquid for the mixing according to step a) is either performed directly or indirectly, in particular via one or more tanks, for temporary storage of the residual liquid.

Generally, the process according to the invention is carried out continuously or semi-continuously, whereby it is additionally differentiated from processes operated batchwise, as are disclosed for instance in GB 2 230 004. "Semi-continuous" in this case designates processes which are operated continuously in principle, but in which the addition of fermentation material does not proceed uninterruptedly, but in time intervals.

In addition, the fermentation in the process according to the invention—in a further contrast to GB 2 230 004—is preferably carried out in a horizontal fermenter, as is likewise described further below.

According to a particularly preferred embodiment, the solids separation according to step c) is performed by means of filtration and/or by means of screening. The residual liquid is thus formed according to this embodiment by the filtrate of the filtration or the screen underflow of the screening.

In addition, it can be preferred to temporarily store the press water obtained in step b) and/or the residual liquid obtained in step c), in particular the filtrate, before the respective following step. This permits the amount of residual liquid that is to be added to be apportioned exactly and in real time, and thereby adapted to the fermentation material present and/or the dry matter proportion thereof, which is of importance, precisely in view of the inhomogeneity of the freshly fed fermentation material.

Generally, the fermentation material is mixed in a mixing device with the residual liquid before the fermentation material suspension obtained in this manner is introduced into the fermenter. According to this embodiment, the fermentation material suspension is thereby premixed outside the fermenter before it is introduced into the fermenter. Alternatively thereto, it is also possible that the mixing proceeds in the fermenter, in particular that the mixing device represents a part of the fermenter.

According to requirements, in addition to the residual liquid used, optionally further water can be fed, which, in the context of the present invention, to distinguish it from the recirculated water of the residual liquid, is denoted fresh water.

Preferably, the dilution of the fermentation material according to step a) is carried out in such a manner that the dry matter proportion in the fermentation material suspension is between 25 and 35.% by weight. The liquid fraction is thereby sufficiently high in order to ensure optimum transportability. At the same time, the dry matter proportion is sufficiently high in order to maximize the fermentation material throughput.

As mentioned, recirculating the residual liquid, in particular the filtrate, firstly serves for diluting the fermentation material, but not the inoculation. The inoculation is preferably achieved via partial recirculation of the digest, of the press cake obtained during the dewatering according to step b) and/or of the residual solid obtained in the solids separation in step c) as inoculum material. In this respect, it is also conceivable to recirculate a mixture of at least two of these fractions as inoculum material.

Although the aim of recirculating the residual liquid, in particular the filtrate, firstly serves for dilution, in some circumstances it may be advisable to determine one or more of the following parameters and, proceeding therefrom, to set it to a desired value:

pH,
buffer capacity,
$H_2S$ content,
ammonium ion content or ammonia content,
content of fatty acids and
content of short-chain carboxylic acids.

In order to obtain the desired value, it can therefore be preferable to add the following auxiliaries or additives to the residual liquid alone or in a mixture:

acid,
lye,
buffer,
micronutrient elements or trace elements and
macronutrient elements.

By this adjustment of various parameters of the residual liquid, the fermentation material suspension can thereby be optimally matched to the fermentation processes proceeding in the fermenter.

As mentioned, the solids separation according to step c) can be carried out by means of filtration. In this respect, it has been found that the filtration can be carried out using a vertical filter device that comprises a hollow-cylindrical filter column having a perforated cylinder shell surface, a screw conveyor arranged concentrically in the filter column and rotating axially around the cylinder axis, and also a filtrate chamber arranged outside the filter cylinder, in which a reduced pressure for drawing in the filtrate is generated. Therein, the press water from the bottom end of the screw conveyor is transported along the inner surface of the filter column upwards in the direction of a solids discharge and filtrate is taken off through the filter openings into the filtrate space at reduced pressure. An example of such a filter device is, for instance, a helical filter.

With respect to efficiency and properties of the filtrate obtained, however, it is particularly preferred that the solids separation according to step c) proceeds by means of a screen, in particular by means of a vibrating screen and/or a shaking screen. Generally, the vibrating screen in this case has two or more screening stages, i.e. two screen cloths, that differ from one another in mesh width. In this case, in a first screening stage c1), a coarse fraction of solids components is separated off from the press water and from the suspension remaining from the stage c1) as screen underflow, in a subsequent second screening stage c2), a fine fraction is separated off in order to obtain the residual liquid. Typically, the vibration movement of the screen container or of the screen containers is obtained by means of an eccentrically arranged drive shaft or by means of a flywheel mass eccentrically arranged on a drive shaft.

It has surprisingly been found that, using the described vibrating screen, a dry matter proportion of at most 15% by weight in the residual liquid may be achieved without problems. The vibrating screen to be used in accordance with this embodiment is, in particular, superior to a non-moving membrane filter as solids separator, since a blockage of the screen cloth can be effectively counteracted and thereby continuous operation of the plant can be ensured. Furthermore, with respect to efficiency of the process and properties of the residual liquid, in particular with respect to the dry matter proportion thereof, even better results are achieved using a vibrating screen than using a helical filter.

Apart from the above described process, the present invention additionally relates to a plant for carrying out the process.

By analogy with the above description of the process, the plant comprises

A) a fermenter for carrying out the anaerobic fermentation and
B) a dewatering device for dewatering the digest, which dewatering device is connected to the fermenter via a digest feed line.

According to the invention, the plant additionally comprises

C) a solids separator that is connected to the dewatering device via a press water feed line and is for separating off residual solid from the press water obtained in the dewatering device, wherein the solids separator is designed in such a manner that the residual liquid obtained here has a dry matter proportion of at most 15% by weight, and
D) a residual liquid feed line for the at least partial recirculation of the residual liquid into the fermenter.

As likewise mentioned above, the solids separator, according to a particularly preferred embodiment, is a filtration device and/or a screen that is designed in such a manner that the resultant filtrate or the resultant screen underflow has a dry matter proportion of at most 15% by weight.

By analogy with the above descriptions relating to the process according to the invention, the plant according to the invention also differs from that according to EP-A-1 095 924, which is designed to use press water as inoculant and therefore does not comprise a solids separator C).

It is further preferred that the fermenter is oriented at least approximately horizontally, whereby it very obviously differs from the fermenter disclosed in GB 2 230 004, which is directed towards a process operating batchwise.

It is further preferred that the residual liquid feed line opens out into a mixing device for mixing the fermentation material with liquid, which mixing device is connected via a feed line to the fermenter. The premixing is therefore carried out in this preferred embodiment of the plant in a device separate from the fermenter. The recirculation to the fermenter therefore proceeds not directly, but indirectly via said mixing device.

For the abovementioned case, that the solids separator is a filtration device, the filtration device preferably comprises C1) a hollow-cylindrical filter column having a perforated cylinder shell surface,
C2) a screw conveyor arranged concentrically in the filter column and rotating axially around the cylinder axis and
C3) a filtrate chamber arranged outside the filter cylinder, to which filtrate chamber means are assigned for generating a reduced pressure for drawing in the filtrate.

As described above, by such a filtration device, in particular by a helical filter, particularly advantageous filtrates may be obtained relatively simply for the purposes of the invention.

The invention is illustrated further with reference to the figures. Of these:

Figure 1:
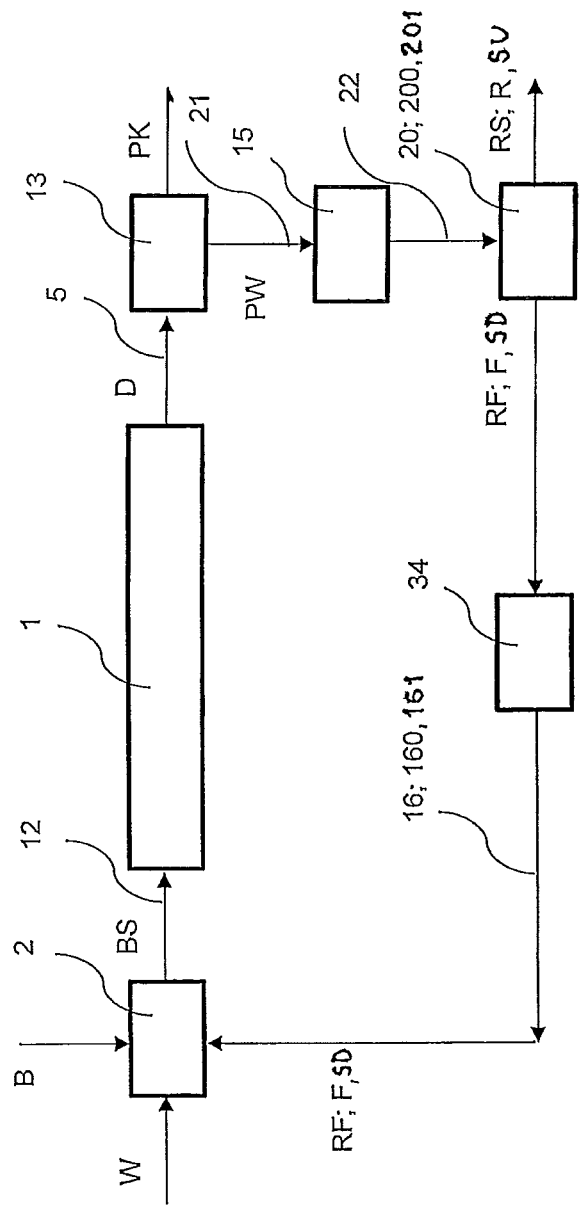
FIG. 1 shows a flow diagram of the process according to the invention.

The specific process shown in FIG. 1 according to the present invention comprises the steps that the biogenic waste materials that are to be fermented anaerobically are fed as fermentation material B into a mixing device 2.

Liquid is introduced into the mixing device 2 in order to set the desired homogeneity and the desired dry matter proportion of the fermentation material suspension BS that is to be fermented. At least a part of the liquid that is fed is fed to the mixing device in the form of a filtrate F, the provision of which is described in detail further below. A further part of the liquid can be fed to the mixing device 2 in the form of fresh water W.

The mixing device can be designed, for instance, in an analogous manner, as described in EP-A-1 076 051 in paragraphs [0020] and [0021], the contents of which are hereby incorporated by reference.

The fermentation material suspension BS generated in the mixing device 2 has a dry matter proportion in the range from 25 to 35% by weight and is fed via a feed line 12 to a fermenter 1. The feed proceeds here continuously or semi-continuously and determines the time of passage through the fermenter of the fermentation material suspension BS. Alternatively to the embodiment shown, in which the mixing device 2 is a device separate to the fermenter 1, the mixing of the fermentation material B with additional liquid can also be carried out in the fermenter.

The digest D which is produced in the fermentation of the fermentation material suspension BS and is at least virtually completely fermented, and the dry matter proportion of which in this specific case is still in the range from 20 to 30% by weight, is finally fed via a digest feed line 5 to a dewatering device 13 and dewatered by means of said dewatering device, wherein, with separation of press water PW, a press cake PK is obtained which has a dry matter proportion which is increased with respect to the digest D. Specifically, the dry matter proportion of the press cake PK is in the range from 30 to 40% by weight, whereas the dry matter proportion of the press water PW in the specific case is between 15 and 20% by weight.

The press water PW obtained in this manner is then fed to a solids separator 20 in the form of a filtration device 200 or a screen 201, wherein, as residual liquid RF, a filtrate F or a screen underflow SD having a dry matter proportion reduced in comparison with the press water PW of at most 15% by weight, specifically a dry matter proportion in the range from 5 to 15% by weight, is obtained, whereas the retentate R or the screen oversize SU produced as residual solid RS of the filtration has a dry matter proportion in the range from 35 to 45% by weight.

As previously mentioned, finally, the filtrate F and/or the screen underflow SD is recirculated to the mixing device 2, where it is used for homogenizing the fermentation material B and for setting the desired dry matter proportion.

In the embodiment specifically shown, the press water PW obtained in the dewatering is fed via a first press water feed line section 21 to a press water tank 15, in which it is stored temporarily before it is passed via a second press water feed line section 22 to the filtration device 200. In addition, the filtrate F obtained in the filtration is also stored temporarily in a filtrate tank 34 before it is recirculated via a residual liquid feed line 16 in the form of a filtrate feed line 160 to the mixing device 2. Of course, it is also conceivable that the press water PW and/or the filtrate F or the screen underflow SD is fed directly, that is to say without temporary storage, to the subsequent filtration or mixing device 200 or 2, respectively.

The plant according to the invention is described further hereinafter with reference to FIG. 2.

Figure 2:
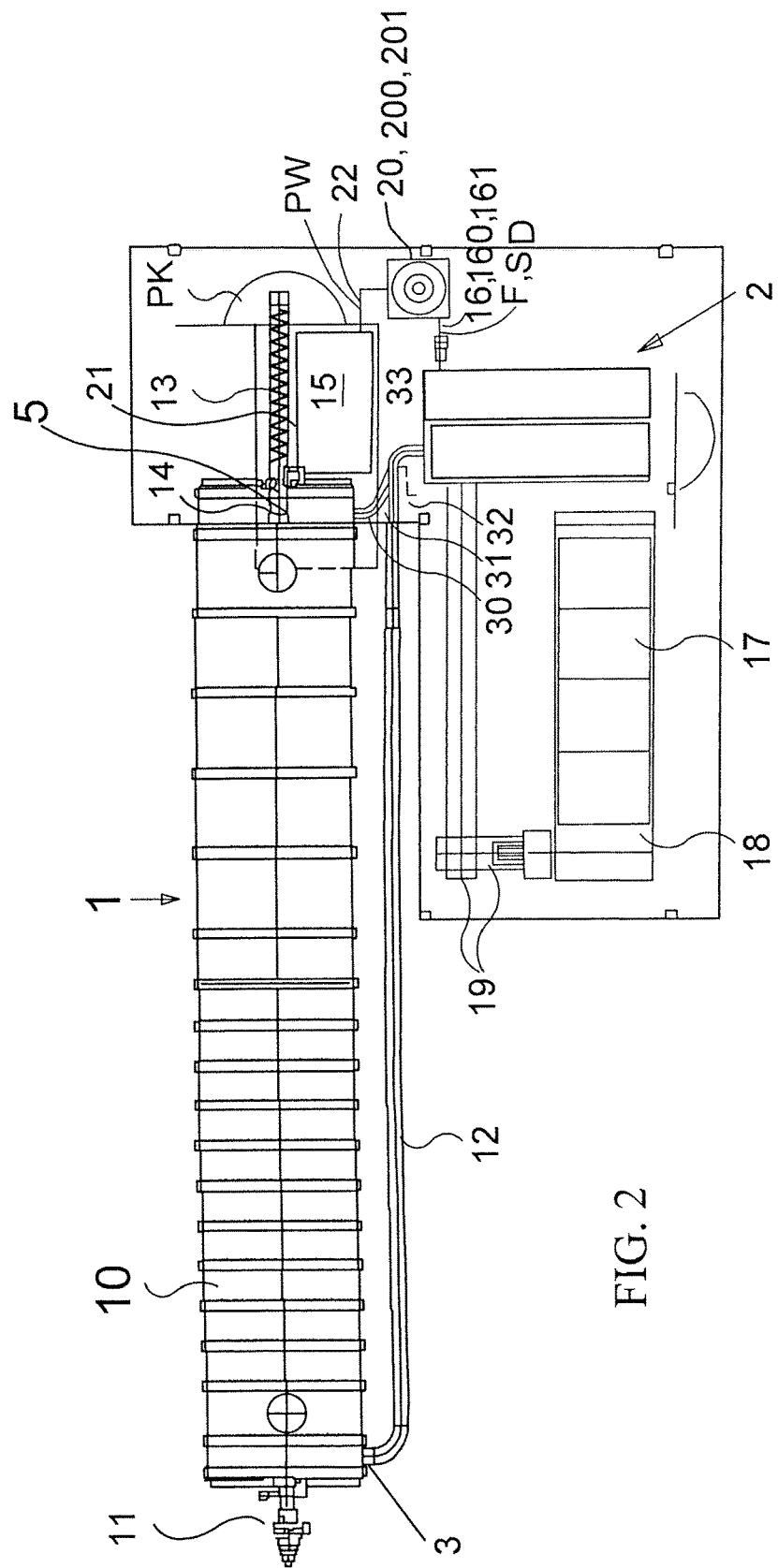
FIG. 2 shows a schematic representation of a plant according to the invention.

In the embodiment shown specifically in FIG. 2, the fermenter 1 comprises a horizontal fermenter tank 10.

The fermenter tank 10 can either be configured as a steel structure or as a lined concrete structure and extends in the axial direction from a first inlet-side end 101 to a second outlet-side end 102. An agitator passes axially through the fermenter tank 10, which agitator is intended to mix thoroughly fermentation material introduced via a fermenter inlet 3 while said fermentation material passes through the fermenter tank 10 in the direction towards a fermenter outlet 14. An agitator drive 11 is assigned to the agitator, which agitator drive is arranged at the inlet-side end of the fermenter tank 10.

The fermentation material is fed in via a preferably heatable feed line 12 which at one end is connected to the fermenter inlet 3 and which at the other end is coupled to a mixing device 2 that is described in connection with FIG. 1, and in which the fermentation material suspension that is to be fed in is prepared.

As mentioned in connection with FIG. 1, the feed-in is continuous or semi-continuous. Likewise, the passage through the fermenter 1 proceeds continuously or semi-continuously.

Via the fermenter outlet 14, the at least virtually completely fermented digest arrives into a dewatering device 13 for dewatering the digest. While the press cake PK obtained via the dewatering is fed to a secondary digestion, the press water PW is fed via a first press water feed line section 21 to a press water tank 15 and there stored temporarily. Via a second press water feed line section 22, press water is fed from the press water tank 15 to a solids separator 20 in the form of a filter device 200 or a screen 201, in which the press water is filtered, such that the filtrate F or screen underflow SD obtained as residual liquid has a dry matter proportion of at most 15% by weight.

From the filter device 23, the filtrate F or the screen underflow SD is fed via a residual liquid feed line 16 in the form of a filtrate feed line 160 or screen underflow feed line 161, respectively, to the mixing device 2, which in addition is charged with fresh fermentation material that is to be treated.

The mixing device 2 is here charged, not as is customary from an intermediate bunker inside the building, but rather the fresh fermentation material passes directly from the delivery to a metering conveyor 17, from which the fermentation material passes via a discharge unit 18 to a conveyor belt 19 opening out into the mixing device.

Customarily, waste materials that are to be fermented are comminuted before they are fed to the fermenter. For this purpose, comminuters can be used that are not shown here. Instead of comminuting the waste materials to a suitable size, the fermentation material can also be freed from excessively large components by screening, for example in a drum screen.

The mixing device 2 is connected via a connection line 33 to a fermenter return line 30 and secondly to the feed line 12, wherein the fermenter return line 30 may be opened and closed by means of a slider 31. Also, a slider 32 is assigned to the feed line 12 for opening and closing. Therefore, when the slider 31 is open digest from the fermenter 1 can be introduced into the connection line 33. This digest thus arrives back at the inlet-side end of the fermenter tank, where it is used as inoculum material for the fermentation process.

Figure 3:
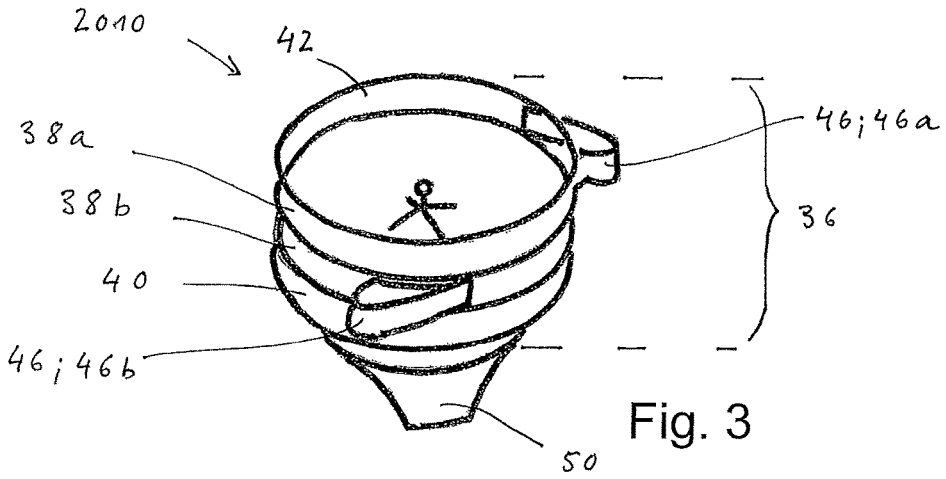
FIG. 3 shows a solids separator particularly suitable for the purposes of the present invention, in perspective view.
Figure 4:
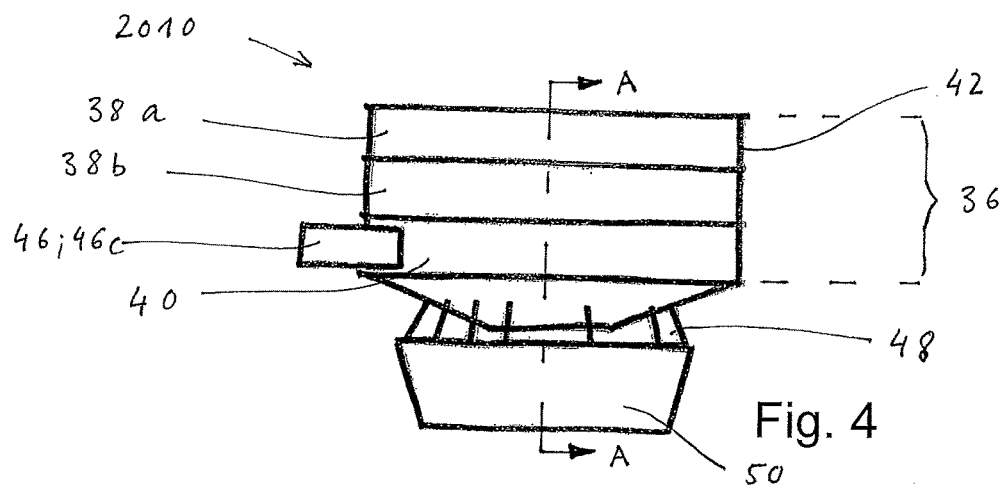
FIG. 4 shows the solids separator shown in FIG. 3 in side view.
Figure 5:
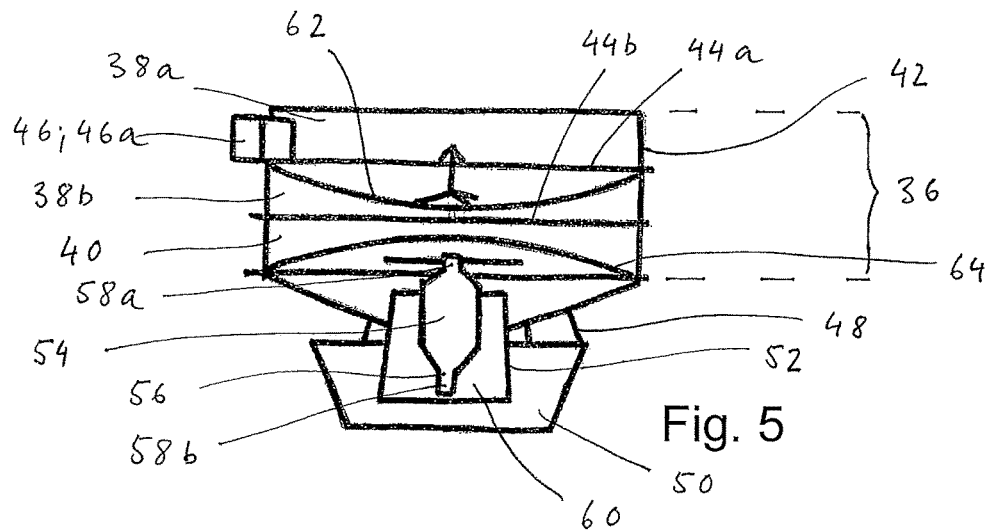
FIG. 5 shows a section through the solids separator shown in FIGS. 3 and 4, through the section planes A-A according to FIG. 4.

A solids separator that is particularly highly suitable for the purposes of the present invention is the vibrating screen 201 shown in FIGS. 3 to 5.

The vibrating screen 2010 comprises a screen unit 36 containing two screen containers 38a, 38b, that are stacked one above the other, and which are arranged on a screen underflow container 40. The screen containers 38a, 38b and the screen underflow container 40 have a substantially circular, identical cross section and are delimited towards the outside via a shell wall 42 running in the peripheral direction.

As proceeds, in particular, from FIG. 5, the first screen container 38a, considered from the top, that is to say considered in the direction of screening, has a first screen cloth 44a which has a larger mesh width than the second screen cloth 44b of the subsequent second screen container 38b. Not only the screen containers 38a, 38b, but also the screen underflow container 40 has an outlet 46 radially projecting from the respective shell wall 42.

The screen unit 36 is supported via corresponding spring elements 48 on a pedestal 50. In addition, a drive housing 52 having a drive 54 is arranged on the screen unit 36, which drive has a drive shaft 56, on the end regions 58a, 58b of which in each case an eccentric flywheel mass 60 sits.

During operation, the screen unit 36 is therefore put into a circular vibration movement. As a result, the press water applied to the first screen contains 38a is constantly agitated, wherein, in particular, the solids components of the press water that are settling on the surface of the first screen cloth 44a are also constantly agitated, and blockage of the screen cloth is effectively prevented.

The screen oversize containing a coarse fraction of solids components is then removed via the coarse fraction outlet 46a, while the screen underflow still containing a fine fraction of solids components is collected in a dished tank 62 arranged beneath the first screen cloth 44a and fed to the second screen cloth 44b.

A screen oversize containing the fine fraction, which screen oversize is removed via the fine fraction outlet 46b, and a residual liquid having a greatly reduced dry matter proportion of at most 15% by weight result from the screening in the second screen container 38b. This residual liquid flows via an upwardly dished base of the screen underflow container at the edge thereof, from where it is ultimately removed from the screen unit 36 via the residual liquid outlet 46c and is recirculated to the fermenter.

LIST OF REFERENCE SIGNS

1 Fermenter
2 Mixing device
3 Fermenter inlet
5 Digest feed line
10 Fermenter tank
11 Agitator drive
12 Feed line
13 Dewatering device
14 Fermenter outlet
15 Press water tank
16; Residual fluid feed line;
160; 161 Filtrate feed line; screen underflow feed line
17 Metering conveyor
18 Discharge unit
19 Conveyor belt
20; Solids separator;
200; Filter device;
201; 2010 Screen; vibrating screen
21 First press water feed line section
22 Second press water feed line section
23 Filter device
24 Filtrate feed line
30 Fermenter return line
31 Slider in fermenter return line
32 Slider in feed line
33 Connection line
34 Filtrate tank
36 Screen unit
38a, 38b Screen containers
40 Screen underflow container
42 Shell wall
44a, 44b Screen cloth
46a, 46b, 46c Outlet
48 Spring elements
50 Pedestal
54 Drive
56 Drive shaft
58a, 58b End regions of the drive shaft
60 Eccentric flywheel mass
62 Tank
64 Base of the screen underflow container
101 Inlet-side end of the fermenter tank
102 Outlet-side end of the fermenter tank
B Fermentation material
BS Fermentation material suspension
D Digest
PW Press water
PK Press cake
RF; F, SD Residual liquid; filtrate, screen underflow
RS; R, SU Residual solids; retentate, screen oversize

The invention claimed is:

1. A process for the anaerobic fermentation of biogenic waste materials, comprising:
    a) mixing a liquid with a fermentation material containing the waste materials to obtain a fermentation material suspension, and anaerobically fermenting the fermentation material suspension in a fermenter to produce a digest;
    b) dewatering the digest by means of a dewatering device to obtain a press water and a press cake having a dry matter proportion increased with respect to the digest; and
    c) subjecting the press water to a solids separation to obtain a residual liquid having a dry matter proportion reduced with respect to the press water, the dry matter proportion of the residual liquid being at most 15% by weight,
    wherein the residual liquid is used at least in part for the mixing according to step a).

2. The process as claimed in claim 1, performed continuously or semi-continuously.

3. The process as claimed in claim 1, wherein the solids separation according to step c) is performed by means of filtration and/or by means of screening, and the residual liquid is formed by the filtrate of the filtration or by the screen underflow of the screening.

4. The process as claimed in claim 1, wherein the press water obtained in step b) and/or the residual liquid obtained in step c) is temporarily stored before the respective following step.

5. The process as claimed in claim 1, wherein step a) comprises mixing the fermentation material in a mixing device with the residual liquid and optionally further water to obtain the fermentation material suspension.

6. The process as claimed in claim 1, wherein the dry matter proportion in the fermentation material suspension in step a) is between 25 and 35% by weight.

7. The process as claimed in claim 1, wherein a part of the digest, the press cake obtained during the dewatering according to step b), the residual solids obtained in the solids separation in step c), or a mixture thereof is added to the fermentation material or the fermentation material suspension as inoculum material.

8. The process as claimed in claim 1, further comprising determining and setting to a desired value one or more parameters of the residual liquid, said parameters being selected from the group consisting of:
pH,
buffer capacity,
$H_2S$ content,
ammonium ion content or ammonia content,
content of fatty acids, and
content of short-chain carboxylic acids.

9. The process as claimed in claim 1, further comprising adding at least one of the following auxiliaries or additives to the residual liquid:
acid,
lye,
buffer,
micronutrient elements or trace elements, and
macronutrient elements.

10. The process as claimed in claim 3, wherein the solids separation according to step c) is performed by means of screening having two or more screening stages, wherein, in a first screening stage c1), a coarse fraction of solids components is separated off from the press water and from the suspension remaining from the stage c1) as screen underflow, in a subsequent second screening stage c2), a fine fraction is separated off in order to obtain the residual liquid.

11. The process as claimed in claim 1, wherein the solids separation according to step c) is performed using a vibrating screen and/or a shaking screen.

12. The process as claimed in claim 10, wherein the solids separation according to step c) is performed using a vibrating screen and/or a shaking screen.

* * * * *